United States Patent [19]

Laufbahn

[11] 4,073,295

[45] Feb. 14, 1978

[54] CATHETER

[75] Inventor: Jennie Laufbahn, Bronx, N.Y.

[73] Assignee: Henry A. Schon, Brooklyn, N.Y.; a part interest

[21] Appl. No.: 685,884

[22] Filed: May 12, 1976

[51] Int. Cl.² ............................................... A61F 5/44
[52] U.S. Cl. .................................................... 128/295
[58] Field of Search ................................. 128/294, 295

[56] References Cited

U.S. PATENT DOCUMENTS

| 2,252,672 | 8/1941  | McLeod  | 128/295 |
| 2,610,630 | 9/1952  | Crew    | 128/295 |
| 3,032,038 | 5/1962  | Swinn   | 128/295 |
| 3,353,538 | 11/1967 | Carrigan | 128/295 |

Primary Examiner—Robert W. Michell
Assistant Examiner—Henry S. Layton

[57] ABSTRACT

A catheter for males including a flexible, resilient, sheath-like bag for reception of the penis and provided with a thickened upper end portion or rim supported from a waist encircling belt by a pair of elongated resilient straps which are capable of being adjustable in length. The lower end of the bag is communicated with a leg supported urine collection bag. The upper end portin or rim of the flexible bag or sheath-like tubular member is provided with a plurality of integrally formed loops or slot-like openings for receiving the reversely folded lower end portion of the straps or a double headed button for securing the lower ends of the straps adjustably to the bag.

1 Claim, 6 Drawing Figures

U.S. Patent  Feb. 14, 1978  4,073,295
Fig. 1
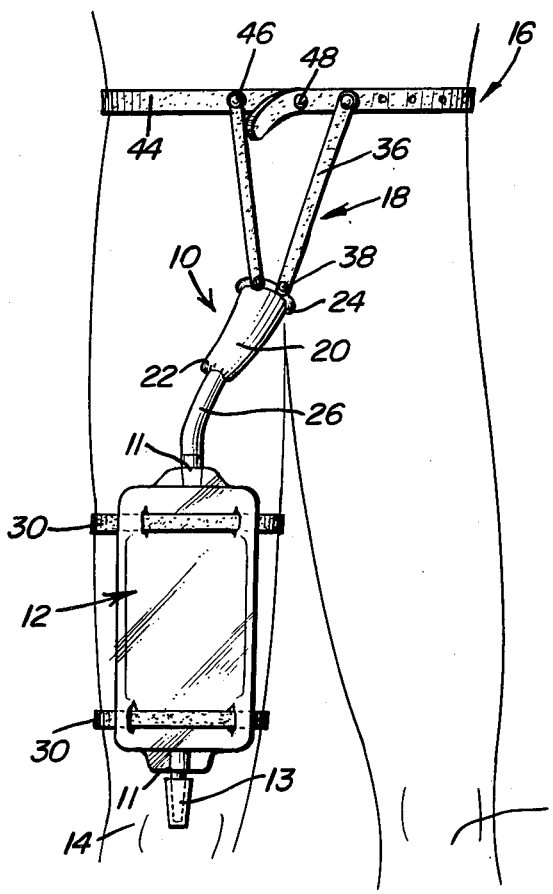
Fig. 2
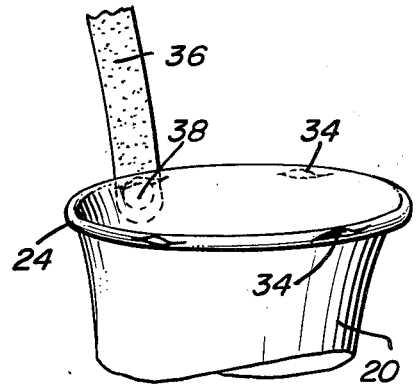
Fig. 3
Fig. 4
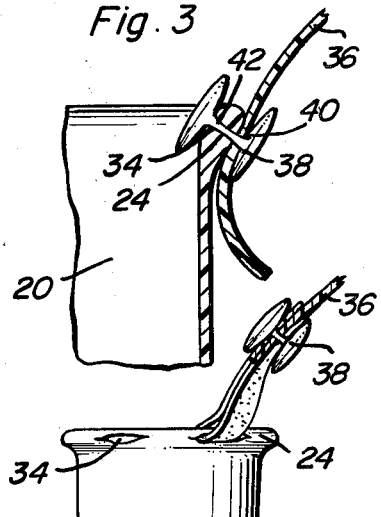
Fig. 5
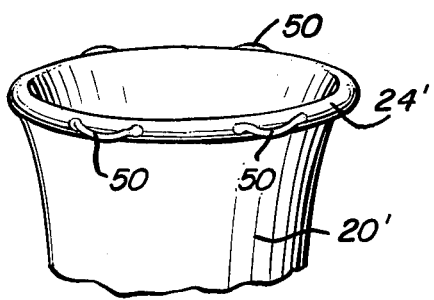
Fig. 6
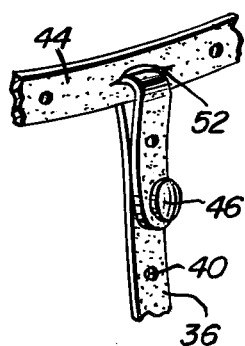

CATHETER

BACKGROUND OF THE INVENTION

1. Field of the Invention

The present invention generally relates to a catheter and more particularly to a catheter of the type which is positioned externally and telescopically on the penis of the person using the device with the bag being provided with novel and unique structural features which enables it to be supported effectively from a waist encircling belt by a pair of adjustable, elastic straps.

2. Description of the Prior Art

Conventionally, a catheter includes a flexible tube which is inserted into the urethra, along the urinary tract into the bladder with the outer end of the tube being connected to a urine collecting bag supported at an elevation lower than the bladder for urine drainage and collection. This type of catheter, usually referred to as a "Foley" catheter, includes an expandable portion which is expanded after insertion for retaining the tube in place. The insertion of this type of catheter usually requires the services of a trained professional person and is sometimes quite painful. Also, in order to avoid infection, this type of catheter must be frequently irrigated and it usually must be replaced on a monthly basis, usually by a urologist. In many instances, the insertion of this type of catheter is not necessary. For example, if a patient does not have any blockage but has merely lost the capability of controlling discharge of urine from the bladder, it is not necessary nor is it desirable to insert this type of catheter.

Recently, a new type of catheter has been marketed by Porges Catheter Corp., New York, New York, in the form of a flexible, resilient, sheath-like bag or tubular member shaped to conform with and to be rolled onto a penis with the lower end of the bag being communicated with a urine collecting bag which usually has a flutter type entrance valve and is supported on the leg of the wearer. One manufacturer of this type bag is Resiflex Laboratory, Covina, California. The open upper end of the sheath-like bag is secured to the penis adjacent the surface of the body by the use of an adhesive tape and the lower end has a small tube thereon extending into the upper end of the collection bag. When applying this structure, the adhesive tape which engages the upper end of the resilient bag or sheath must be pulled tight in order to retain the device in place. This frequently causes extreme discomfort and swelling due to restriction of circulation of body fluids and, in some instances, even restricts the flow of urine through the urethra. While this device eliminated the necessity of having a skilled professional apply the catheter, it usually required the services of a person in addition to the person wearing the device in order to properly apply it and unless extreme care is used, the adhesive could contact the surface of the skin which causes irritation thereof which sometimes becomes infected and in other instances, the adhesive tape was too tightly applied, thus defeating the purpose of the catheter and also causing discomfort and pain.

SUMMARY OF THE INVENTION

An object of the present invention is to provide a catheter which comprises a thin, highly flexible and resilient, sheath-like tubular member, generally in the form of a condom, adapted to receive the penis of a male patient with the open upper end thereof having a plurality of integral loops, slot-like or buttonhole-type openings formed in a thickened or denser end portion for supporting the sheath-like tubular member or bag on the penis without constriction by a pair of adjustable length elastic straps extending upwardly with their upper ends secured to a waist encircling belt, thereby facilitating assembly of the catheter and enabling it to be worn without discomfort or pain and enabling adjustment of the supporting structure to enable the catheter to be adjusted in order to custom fit the wearer.

Another object of the invention is to provide a catheter in accordance with the preceding object in which the waist encircling belt is in the form of an adjustable length elastic strap and each of the supporting straps is in the form of an adjustable length elastic strap of latex rubber, plastic or the like, thus enabling the catheter to be inexpensively manufactured and easily adjusted.

Still another object of the invention is to provide a catheter in which a flexible resilient bag is effectively supported in position to receive urine from the urethra of a patient with the lower closed end of the bag having an adapter for connection with a leg supported collection bag thereby enabling the wearer to walk normally and perform various activities without hinderance.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a front elevational view of the catheter of the present invention illustrating the association of the components thereof when in use.

FIG. 2 is an enlarged perspective view of the upper end of the catheter illustrating the construction of the embodiment of the invention in which four slots are formed in the upper end of the bag for connection with the flexible resilient supporting straps.

FIG. 3 is a vertical sectional view of the connection between the strap and bag as illustrated in FIG. 2.

FIG. 4 is a side elevational view of the catheter, with the lower portion being shown in section, and illustrating another manner of attaching the supporting straps to the catheter.

FIG. 5 is a perspective view, similar to FIG. 2, but illustrating an embodiment of the invention in which four integral loops are formed on the thickened upper end of the bag.

FIG. 6 is a fragmental perspective view of the waist belt and manner of attaching a supporting strap thereto.

DESCRIPTION OF THE PREFERRED EMBODIMENTS

Referring now specifically to the drawings, the catheter of the present invention is generally designated by reference numeral 10 which is associated with a urine collecting bag generally designated by numeral 12 which is supported on the leg 14 of a person using the catheter. The catheter 10 is supported from a waist encircling belt generally designated by numeral 16 by a pair of adjustable length straps generally designated by numeral 18.

The catheter 10 includes an elongated sheath-like tubular member or bag 20 which is constructed of very thin, highly flexible and thin rubber or other similar material and generally is in the form of a condom having a closed lower end 22 and a thickened rib or dense area 24 at the upper end thereof with the bag 20 generally conforming with and receiving the penis of a male user with the bag being assembled on the penis in a conventional and well-known manner. The lower closed end 22 of the bag 20 is provided with a discharge tube 26 which is sufficiently rigid to maintain its shape and to provide a passageway 28 to the urine collecting bag 12 which also may be constructed of plastic material and secured to the leg 14 by a pair of straps 30 in a conventional manner and includes a more rigid tapered tube 11 having reducing diameter shoulders at each end thereof with the upper end tube receiving tube 26 and the lower tube receiving a cap 13 telescoped thereon and held in place by friction to facilitate emptying of the bag. The urine collecting bag 12 and its supporting straps as well as the tubular member 26 and its connection to the bag 20 and the bag 20 to the extent described above all are commercially available products with the present invention being directed to the structural modifications of the bag 20 and the manner of supporting the bag 20 as compared with the conventional procedure which involved the use of an adhesive tape wrapped around the upper end portion of the bag 20 and the penis adjacent its juncture with the body surface of the wearer.

The supporting structure includes a modified construction of the bag 20 and particularly the thickened upper end portion 24 thereof. In one embodiment of the invention, the thickened upper end 24 of the bag 20 is provided with four circumferentially spaced slots 34 or punched holes generally in the form of buttonholes which are formed in the bag when it is being constructed or the slots or holes can be formed therein after formation of the bag. The thickened or more dense upper end portion 24 provides adequate strength characteristics to enable the outermost pair of slots 34 to be used for connecting the two straps 18 thereto. The straps 18 are relatively narrow elastic straps of latex or the like as designated by numeral 36 and are connected to the slots 34 by a double headed button 38 having one portion inserted through the slots 34 and another portion inserted through one of a series of longitudinally spaced openings 40 formed in the strap 36. The relatively small shank portion 42 of the button 38 is received in the slot-like opening 34 and in the aperture 40 in the strap 36 as illustrated in FIG. 3, thereby adjustably supporting the bag 20 from two of the straps 36 which extend upwardly and diverge outwardly slightly and are connected to an elastic belt 44 by buttons 46 which are identical to the buttons 38. Also, the waist encircling belt 16 is in the form of a strap or belt 44 of resilient material, such as latex, and provided with a plurality of apertures longitudinally spaced along the length thereof with the overlapping ends of the belt 44 also being connected together adjustably by a belt 48. Thus, with this construction, the catheter 20 may be custom fitted to the wearer and the elastic straps 36 provide a comfortable but yet dependable support for the bag 20 and the support and the bag will not interfere with any normal body functions and will not cause pain or discomfort to the wearer.

FIG. 4 illustrates another supporting arrangement in which the strap 36 rather than being connected directly to the slot 34 by a button 38 as illustrated in FIGS. 2 and 3, is connected to the slots 34 by extending the lower end portion of the strap 36 through one of the slots 34 and doubling it back upon itself with the free end portion of the strap 36 then being secured in place by a button 38 extending through aligned apertures in the vertical elongated portion of the strap 36 and the reversely looped portion of the strap 36, thereby enabling the button 38 to be positioned away from the upper end portion 24 of the bag and away from the adjacent surface portions of the penis and patient's body, thereby further enhancing the comfort of the device when being used.

FIG. 5 illustrates another embodiment of the invention in which the bag is designated by numeral 20' and the upper thickened or denser end portion is designated by numeral 24'. Formed integrally with the denser or thickened end portion 24' is a plurality of loops 50 spaced circumferentially around the upper end portion 24' in the same manner as the slots 34 are positioned in FIGS. 1-4. With this construction, the lower end of the strap 36 may be threaded through a loop 50 and secured adjustably in the manner illustrated in FIG. 4. As in the embodiment illustrated in FIGS. 1-4, the two straps 36 will be engaged with the two outer loops, thus assuring that no uncomfortable irritation will occur since the entire attaching and supporting structure will be oriented outwardly of and away from the skin surface.

FIG. 6 illustrates an alternative structure for connecting the upper end of the straps 36 to the waist encircling belt or strap 44 in which the belt 44 is provided with slots 52 as well as small openings therethrough thus enabling the straps 36 to be threaded through the slot 52 and reversely folded and secured in adjusted position by a button 46, thereby further facilitating adjustment of the length of the supporting straps 18 and orienting the button 46 away from the belt 44 thereby precluding the belt 44 from pulling the button into contact with the skin surface of the wearer.

The thickened top roll or end portion 24 or 24' provides the requisite strength for the slots 34 or the loops 50. The straps 36 and the belt strap 44 are of the same construction and are commercially available products used for supporting various medical appliances in relation to a patient's body and are constructed of resilient material, such as latex rubber, or the like, having a plurality of longitudinally spaced holes or slots therein which may be stretched and enlarged for positioning a button or other suitable fastener therethrough in a well-known manner. Similar types of straps are used in order to hold the collection bag 12 in position. With this construction, various adjustment features may be incorporated into the device and by properly fitting the device to each individual wearer, the catheter will be painless and will not introduce discomfort to the patient. The catheter also will not interfere with normal body functions, thus enabling the person using the device to walk and perform other necessary duties without problems relating to wetness or odor caused by urine discharged. The inexpensive construction of the device enables it to be economically disposable and it is easy to remove and easy to place in position by the person using the device without assistance.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A catheter comprising a flexible, resilient and thin tubular member defining a sheath-like bag positioned in enclosing relation to a substantial portion of a male wearer's penis, said bag including a closed end portion having a drain tube communicated therewith and extending to a leg attached urine collecting bag, the open end of said sheath-like bag being defined by a thickened end portion, said thickened end portion including attaching means thereon to which a pair of upwardly extending flexible, resilient support straps are attached, a flexible resilient waist belt encircling the waist of the wearer and having the upper ends of the support straps attached thereto thereby supporting the sheath-like bag in place; said attaching means are in the form of two slots disposed outwardly of the body surface of the wearer; said straps being connected to the attaching means by being looped through the slots with the free end of the strap being reversely folded and secured to the main portion of the straps by double headed buttons; and wherein the straps and the waistband are provided with a plurality of small longitudinally spaced openings whereby the straps and the waistband are adjustably connected by double-headed buttons extending through selected openings.

* * * * *